(12) United States Patent
Melnikov

(10) Patent No.: US 11,098,370 B2
(45) Date of Patent: Aug. 24, 2021

(54) METHOD OF DIAGNOSING A DISEASE ACCOMPANIED BY EXCESSIVE CELL DEATH AND KIT FOR THE IMPLEMENTATION THEREOF

(71) Applicant: LIMITED LIABILITY COMPANY "BIOMARKER-RU", Moscow (RU)

(72) Inventor: Anatoly Alexandrovich Melnikov, Moscow (RU)

(73) Assignee: LIMITED LIABILITY COMPANY "BIOMARKER-RU", Moscow (RU)

( * ) Notice: Subject to any disclaimer, the term of this patent is extended or adjusted under 35 U.S.C. 154(b) by 319 days.

(21) Appl. No.: 16/075,310

(22) PCT Filed: Feb. 3, 2017

(86) PCT No.: PCT/RU2017/050004
§ 371 (c)(1),
(2) Date: Aug. 3, 2018

(87) PCT Pub. No.: WO2017/135850
PCT Pub. Date: Aug. 10, 2017

(65) Prior Publication Data
US 2019/0062847 A1 Feb. 28, 2019

(30) Foreign Application Priority Data
Feb. 5, 2016 (RU) .......................... RU2016103685

(51) Int. Cl.
| | |
|---|---|
| *C12Q 1/6886* | (2018.01) |
| *G01N 33/50* | (2006.01) |
| *C12Q 1/48* | (2006.01) |
| *C12Q 1/68* | (2018.01) |
| *G16B 25/20* | (2019.01) |
| *G16B 30/00* | (2019.01) |
| *C12Q 1/6883* | (2018.01) |

(52) U.S. Cl.
CPC .............. *C12Q 1/6886* (2013.01); *C12Q 1/48* (2013.01); *C12Q 1/68* (2013.01); *C12Q 1/6883* (2013.01); *G01N 33/50* (2013.01); *G16B 25/20* (2019.02); *G16B 30/00* (2019.02); *C12Q 2600/112* (2013.01)

(58) Field of Classification Search
CPC .......... C12Q 1/6886; C12Q 1/48; C12Q 1/68; C12Q 1/6883; C12Q 2600/112; C12Q 2600/158; C12Q 1/6851; C12Q 1/6848; C12Q 1/6806; C12Q 1/6818; C12Q 1/686; C12Q 2521/101; C12Q 2537/165; C12Q 2561/113; C12Q 2531/113; C12Q 2527/101; G16B 25/20; G01N 33/50
See application file for complete search history.

(56) References Cited

U.S. PATENT DOCUMENTS

| | | | |
|---|---|---|---|
| 5,972,615 A | 10/1999 | An et al. | |
| 2013/0295576 A1* | 11/2013 | Yamamoto | C12Q 1/6848 435/6.12 |

FOREIGN PATENT DOCUMENTS

RU          2 523 589          7/2014

OTHER PUBLICATIONS

Alicia Rodriquez et al., PCR Primer Design. Methods in Molecular Biology, vol. 1275, Humana Press, New York, NY, Chapter 3, pp. 31-56, Jan. 2015.*
WU et al., Oncology Letters, 16: 3726-3734, (Year: 2018).*
Lamikanra et al., Malaria Journal, 11:201, 1-5, (Year: 2012).*
Sims et al., Physical Therapy, vol. 85, issue 3, pp. 257-268, Mar. 2005.*
Kraemer et al., Tutorial in Biostatistics, Statistics in Medicine, 21:2109-2129, (Year: 2002).*
Khan et al., Indian J. Med Res. 141(1): 13-26, Jan. 2015.*
Belov et al., "Optimisation of RT-PCR Nucleic Acid Quantitative Analysis" *Nauchnoye Priborostroyeniye*, 2011, vol. 21, No. 1, pp. 44-49.
Paepe, Boel De, "Mitochondrial Markers for Cancer: Relevance to Diagnosis, Therapy, and Prognosis and General Understanding of Malignant Disease Mechanisms" *ISRN Pathology*, 2012, Article ID 217162, 15 pages.
International Search Report for PCT/RU2017/050004 dated May 25, 2017, 3 pages.
"The Main Properties of Tumors" Chapter 10, Section 13, p. 35, with English Translation, 3 pages.
Huang et al. "Quantitative analysis of plasma circulating DNA at diagnosis and during follow-up of breast cancer patients" Cancer Letters, 243 (2006), 7 pages.
Garcia-Olmo et al. "Cell-free nucleic acids circulating in the plasma of colorectal cancer patients induce the oncogenic transformation of susceptible cultured cells" Cancer Res. 2010, 70:560-567.
Meng et.al. "Mitochondrial DNA Copy Number Alteration in Human Cancers" North American Journal of Medicine and Science, Jan. 2013, vol. 6, No. 1, 4 pages.
Mehra et. al. "Circulating Mitochondrial Nucleic Acids Have Prognostic Value for Survival in Patients With Advanced Prostate Cancer". Clin Cancer Res. Jan. 15, 2007, vol. 13, No. 2, 7 pages.

(Continued)

*Primary Examiner* — Cynthia B Wilder
(74) *Attorney, Agent, or Firm* — Nixon & Vanderhye P.C.

(57) ABSTRACT

A group of inventions belongs to medicine, specifically to the laboratory diagnostics, and concerns the diagnostics of diseases accompanied by the increased cell death and a kit for its performance. The human blood plasma sample is taken, then the real-time polymerase chain reaction is performed. Coefficient K is calculated on basis value of polymerase chain reaction and it is compared with reference value. A disease accompanied by the increased cell death is diagnosed when value of coefficient K is less than the reference value. The invention group allows to carry out the minimal invasive diagnostics of diseases accompanied by the increased cell death with high sensitivity, at any stages of disease including the early stages, at which the clinical signs are absent.

16 Claims, No Drawings

Specification includes a Sequence Listing.

(56) References Cited

OTHER PUBLICATIONS

Xia et al. "Simultaneous quantitative assessment of circulating cell-free mitochondrial and nuclear DNA by multiplex real-time PCR" Genetics and Molecular Biology, 2009, vol. 32, No. 1, 5 pages.

Breitbach et al. "Direct Quantification of Cell-Free, Circulating DNA from Unpurified Plasma" PLOS ONE, Mar. 2014, vol. 9, Issue 3, 11 pages.

* cited by examiner

METHOD OF DIAGNOSING A DISEASE ACCOMPANIED BY EXCESSIVE CELL DEATH AND KIT FOR THE IMPLEMENTATION THEREOF

This application is the U.S. national phase of International Application No. PCT/RU2017/050004 filed Feb. 3, 2017, which designated the U.S. and claims priority to RU Patent Application No. 2016103685 filed Feb. 5, 2016, the entire contents of each of which are hereby incorporated by reference.

A group of inventions belongs to medicine, specifically to the laboratory diagnostics, and it can be used for diagnostics of diseases accompanied by the increased cell death.

Human blood has nucleic acids (NAs) not associated with the cells and circulating freely in the blood flow. These NAs appear as a result of the cell death (decay) associated with the continuous replacement of old cells with new cells within all organs. In plasma of healthy human, the concentration of freely circulating DNA (cfDNA, cell free DNA) is about 6 ng/ml. Some diseases are accompanied with increased cell death and consequently with increased cfDNA concentration in patient plasma. The examples of such diseases are primarily the oncological diseases as well as some hepatic disorders, in particular, hepatosis [O. V. Zairatyants at el. Pathologic Anatomy, Chapter 1, Cell and Tissue Damage and Death. 2012, 960 p.].

The malignant tumor growth is often accompanied by the increased cell death. The malignant cells die predominantly through necrosis, to a lesser degree through apoptosis; the cellular debris gets to the blood vessels. That is why most of the oncologic patients have the increased cfDNA concentration in blood plasma in comparison with that of healthy individuals. It has been proved that cfDNA of the oncological patients originated from the malignant cells [Huang Z. H. et al. Quantitative analysis of plasma circulating DNA at diagnosis and during follow-up of breast cancer patients. Cancer Lett. 2006, 243:64-70] and what is more, this cfDNA can induce oncogenic transformation of cells under certain conditions [Garcia-Olmo D. C. et al. Cell-free nucleic acids circulating in the plasma of colorectal cancer patients induce the oncogenic transformation of susceptible cultured cells. Cancer Res. 2010, 70:560-567].

The cancer cell energy metabolism differs from that of the healthy cells. There is increase of the anaerobic glycolysis observed in the cancers cells as well as a copy number of mitochondrial DNA (mtDNA) changes with different cancer types (8). The increased mtDNA copy number was found in case of prostate and ovarian cancers, endometrial cancer, thyroid carcinoma, some types of leukemia, colon carcinoma, cerebral cancer, neck cancer, and other cancer forms. To the contrary, the decreased mtDNA copy number was found in case of stomach cancer, hepatic carcinoma, breast cancer, and other cancer forms. Many factors such as age, oxidative stress, tissue specificity and degree of tumor growth influence upon the mtDNA copy number [Meng S. et. al. Mitochondrial DNA copy number alteration in human cancers. NAJ Med Sci. 2013, 6(1):22-25. DOI: 10.7156/najms.2013.0601022].

The oncological diseases diagnostic method and reagent kit for method performing of Company Mitomics Inc. [www.mitomicsinc.com] based on the analysis of mtDNA structure, its mutations including deletions are known. The most developed test of Company Mitomics Inc. is a test for prostate cancer (Prostate Core Mitomics TEST, PCMT). The test sensitivity is 85%, specificity is 92%. The method's disadvantages are as follows: invasiveness, analysis uses the prostate biopsy material, and this is a painful procedure. To obtain the above sensitivity and specificity parameters, the repeated biopsies are required. The Company continues to work on use of the method for diagnostics of other cancer forms.

There are many works on analysis of total cfDNA, individual genes, mtDNA in blood plasma and serum in the literature [Mehra N. et. al. Circulating mitochondrial nucleic acids have prognostic value for survival in patients with advanced prostate cancer. Clin Cancer Res. 2007, 13:421-426; Xia P. et al. (2009). Simultaneous quantitative assessment of circulating cell-free mitochondrial and nuclear DNA by multiplex real-time PCR. Gen. Mol.Biology, 32, 1, 20-24; core-genomics.blogspot.ru/2014/12/extracting-cell-free-dna-from-plasma.html; PLoS One. (2014) Mar. 3;9(3): e87838. doi: 10.1371/journal.pone.0087838. eCollection 2014]. In the work Xia P. et al. analyzed the genomic DNA and mtDNA of healthy donors. The main disadvantage of above and similar works consists of DNA extraction from blood plasma. Since the appearance of biochemical methods of nucleic acids extraction, the researchers know that a loss of DNA part and change of the gene ration take place with extraction. Company Core Genomics compared the kits of different companies and determined that the losses are up to 40% [core-genomics.blogspot.ru/2014/12/extracting-cell-free-dna-from-plasma.html]. The attempts to assess the cfDNA content of patients without preliminary amplification are undertaken [PLoS One. (2014) Mar. 3;9(3): e87838. doi: 10.1371/journal.pone.0087838. eCollection 2014]. But it is impossible to diagnose the disease only by amount of DNA or certain gene in blood plasma as DNA concentration in blood plasma of healthy patient varies within 1.6-23.7 ng/ml, and within 5.1-183 ng/ml for patients as per data of this work.

A task of this group of inventions is to create a diagnostic method for diseases accompanied by the increased cell death and the reagent kit for method performing based on quantification of freely circulating nucleic acid in blood plasma without their prior extraction.

The task was solved by creation of the diagnostic method for the disease accompanied by the increased cell death, which includes the following:

a) blood plasma sampling in humans;
b) isothermic nucleic acids amplification of blood plasma;
c) nucleic acids purification from the reaction mixture produced as per item b);
d) carrying out of nucleic acid quantification by real-time polymerase chain reaction method and determination of the $K$ coefficient in samples, as follows:

$$K = C_1 \text{ or } K = \frac{C_1 + C_2}{2}, \text{ or } K = \frac{C_1 + C_3}{2}, \text{ or } K = \frac{C_1 + C_2 + C_3}{3},$$

$$\text{Where } C_1 = \frac{Ct \text{ for gene coding for glycolysis enzyme}}{Ct \text{ for mitochondrial gene}},$$

$$C_2 = \frac{Ct \text{ for } NC_{018923.2} \text{12th chromosome fragment}}{Ct \text{ for mitochondrial gene}},$$

$$C_3 = \frac{Ct \text{ for M6PRBP gene}}{Ct \text{ for mitochondrial gene}},$$

Ct—value of polymerase chain reaction threshold cycle;
e) comparison of the $K$ coefficient with the reference value;
f) diagnosis of a disease accompanied by increased cell death while the $K$ coefficient value is less than the reference value.

In particular case of implementation, the diagnostic method for the disease accompanied by the increased cell death is characterized by the fact that isothermic nucleic acids amplification of blood plasma is carried out without preliminary nucleic acids isolation from blood plasma.

In particular case of implementation, the diagnostic method for the disease accompanied by the increased cell death is characterized by the fact that isothermic nucleic acids amplification of blood plasma is carried out in the same tube with blood plasma.

In particular case of implementation, the diagnostic method for the disease accompanied by the increased cell death is characterized by the fact that blood plasma nucleic acids include genomic DNA, mitochondrial DNA, messenger RNA, transfer RNAs, microRNA, and exosome nucleic acids.

In particular case of implementation, the diagnostic method for the disease accompanied by the increased cell death is characterized by the fact that this is an oncological disease, which is accompanied by the increased cell death.

In particular case of implementation, the diagnostic method for the oncological disease is characterized by the fact that the oncological disease is selected from the group including breast cancer, colon cancer, pancreatic cancer, thymus cancer, prostate cancer, ovarian cancer, cerebral glioma.

In particular case of implementation, the diagnostic method for the disease accompanied by the increased cell death is characterized by the fact that this is hepatosis, which is accompanied by the increased cell death.

In particular case of implementation, the diagnostic method for the disease accompanied by the increased cell death is characterized by the fact that the reference value is determined as an average value of K coefficient, received with healthy population screening.

In particular case of implementation, the diagnostic method for the disease accompanied by the increased cell death is characterized by the fact that this is a breast cancer, which is accompanied by the increased cell death, and the reference value is equal to 2.

In particular case of implementation, the diagnostic method for the disease accompanied by the increased cell death is characterized by the fact that this is hepatosis, which is accompanied by the increased cell death, and the reference value is equal to 2.

In particular case of implementation, the diagnostic method for the disease accompanied by the increased cell death is characterized by the fact that the glycolysis enzyme is selected from the group including hexokinase, phosphoglucose isomerase, phosphofructokinase, fructose biphosphate aldolase, triosephosphate isomerase, glyceraldehyde phosphate dehydrogenase, phosphoglycerate kinase, phosphoglycerate mutase, enolase, and pyruvate kinase.

In particular case of implementation, the diagnostic method for the disease accompanied by the increased cell death is characterized by the fact that the mitochondrial DNA fragment is selected from the mitochondria gene group including transfer RNA gene, 12S ribosomal gene, 16S ribosomal gene, NADH-dehydrogenase subunit gene, cytochrome oxidase subunit gene, ATP synthase subunit gene, and cytochrome C reductase gene.

In particular case of implementation, the diagnostic method for the disease accompanied by increased cell death is characterized by the fact that the isothermic nucleic acids amplification of blood plasma is carried out using DNA polymerase phi29.

In particular case of implementation, the diagnostic method for disease accompanied by the increased cell death is characterized by the fact that the isothermic nucleic acids amplification of blood plasma is carried out using protein binding with single straight DNA, trehalose, random primers, detergents, deoxynucleoside triphosphates, magnesium chloride.

In particular case of implementation, the diagnostic method for the disease accompanied by the increased cell death is characterized by the fact that the random primers are Random-7 thio.

In particular case of implementation, the diagnostic method for the disease accompanied by the increased cell death is characterized by the fact that the isothermic nucleic acids amplification of blood plasma is stopped by means of ethylene diamine tetraacetate addition into the reaction mixture.

In particular case of implementation, the diagnostic method for the disease accompanied by the increased cell death is characterized by the fact that following the stop of the isothermic nucleic acids amplification of blood plasma, the DNA purification is carried out.

In particular case of implementation, the diagnostic method for the disease accompanied by the increased cell death is characterized by the fact that the DNA purification is performed as follows: proteinase K is added into the reaction mixture, the reaction mixture is incubated for 15 minutes at 550 C temperature, the reaction mixture is processed with DNAzol® BD reagent, DNA is precipitated with isopropanol, and DNA is washed with ethanol.

In particular case of implementation, the diagnostic method for the disease accompanied by the increased cell death is characterized by the fact that the DNA isolated is dissolved within TE buffer and its concentration is determined.

In particular case of implementation, the diagnostic method for the disease accompanied by the increased cell death, as per item 1, is characterized by the fact that the gene coding for glycolysis enzyme is a gene coding pyruvate kinase.

In particular case of implementation, the diagnostic method for a disease accompanied by the increased cell death is characterized by the fact that Ct for pyruvate kinase gene is determined using a pair of oligonucleotide primers and oligonucleotide probe for detection; at that, one oligonucleotide primer has a sequence, which is homologous at least by 90% to SEQ ID NO:1 sequence, the second oligonucleotide primer has a sequence, which is homologous at least by 90% to SEQ ID NO:2 sequence, the oligonucleotide probe for detection has a sequence, which is homologous at least by 90% to SEQ ID NO:3 sequence.

In particular case of implementation, the diagnostic method for a disease accompanied by the increased cell death is characterized by the fact that Ct for pyruvate kinase gene is determined using a pair of oligonucleotide primers and oligonucleotide probe for detection; at that, one oligonucleotide primer has SEQ ID NO:1 sequence, the second oligonucleotide primer has SEQ ID NO:2 sequence, the oligonucleotide probe for detection has SEQ ID NO:3 sequence.

In particular case of implementation, the diagnostic method for a disease accompanied by the increased cell death is characterized by the fact that Ct for $NC_{018923.2}$ 12th chromosome fragment is determined using a pair of oligonucleotide primers and oligonucleotide probe for detection; at that, one oligonucleotide primer has a sequence, which is homologous at least by 90% to SEQ ID NO:4 sequence, the second oligonucleotide primer has a sequence, which is homologous at least by 90% to SEQ ID NO:5 sequence, the oligonucleotide probe for detection has a sequence, which is homologous at least by 90% to SEQ ID NO:6 sequence.

In particular case of implementation, the diagnostic method for a disease accompanied by the increased cell death is characterized by the fact that Ct for $NC_{018923.2}$ 12th h chromosome fragment is determined using a pair of oligonucleotide primers and oligonucleotide probe for detection; at that, one oligonucleotide primer has SEQ ID NO:4 sequence, the second oligonucleotide primer has SEQ ID NO:5 sequence, the oligonucleotide probe for detection has SEQ ID NO:6 sequence.

In particular case of implementation, the diagnostic method for a disease accompanied by the increased cell death is characterized by the fact that Ct for M6PRBP gene is determined using a pair of oligonucleotide primers and oligonucleotide probe for detection; at that, one oligonucleotide primer has a sequence, which is homologous at least by 90% to SEQ ID NO:7 sequence, the second oligonucleotide primer has a sequence, which is homologous at least by 90% to SEQ ID NO:8 sequence, the oligonucleotide probe for detection has a sequence, which is homologous at least by 90% to SEQ ID NO:9 sequence.

In particular case of implementation, the diagnostic method for a disease accompanied by the increased cell death is characterized by the fact that Ct for M6PRBP gene is determined using a pair of oligonucleotide primers and oligonucleotide probe for detection; at that, one oligonucleotide primer has SEQ ID NO:7 sequence, the second oligonucleotide primer has SEQ ID NO:8 sequence, the oligonucleotide probe for detection has SEQ ID NO:9 sequence.

In particular case of implementation, the diagnostic method for a disease accompanied by the increased cell death is characterized by the fact that mitochondrial gene is COX1 gene.

In particular case of implementation, the diagnostic method for a disease accompanied by the increased cell death is characterized by the fact that Ct for COX1 gene is determined using a pair of oligonucleotide primers and oligonucleotide probe for detection; at that, one oligonucleotide primer has a sequence, which is homologous at least by 90% to SEQ ID NO:10 sequence, the second oligonucleotide primer has a sequence, which is homologous at least by 90% to SEQ ID NO:11 sequence, the oligonucleotide probe for detection has a sequence, which is homologous at least by 90% to SEQ ID NO:12 sequence.

In particular case of implementation, the diagnostic method for a disease accompanied by the increased cell death is characterized by the fact that Ct for COX1 gene is determined using a pair of oligonucleotide primers and oligonucleotide probe for detection; at that, one oligonucleotide primer has SEQ ID NO:10 sequence, the second oligonucleotide primer has SEQ ID NO:11 sequence, the oligonucleotide probe for detection has SEQ ID NO:12 sequence.

In particular case of implementation, the diagnostic method for a disease accompanied by the increased cell death is characterized by the fact that the oligonucleotide probe for detection contains fluorescent dye at 5"-end, fluorescence extinguisher at 3"-end.

In particular case of implementation, the diagnostic method for a disease accompanied by the increased cell death is characterized by the fact that fluorescence dye was selected from group, as follows: JOE, FAM, R6 G, ROX, Cy5, Cy5.5, HEX.

In particular case of implementation, the diagnostic method for a disease accompanied by the increased cell death is characterized by the fact that fluorescence extinguisher was selected from group, as follows: BHQ1, BHQ2, BHQ3, RTQ.

In particular case of implementation, the diagnostic method for a disease accompanied by the increased cell death is characterized by the fact that $$K = \frac{Ct \text{ for pyruvate kinase gene}}{Ct \text{ for } COX_1 \text{ gene}}.$$

In particular case of implementation, the diagnostic method for a disease accompanied by the increased cell death is characterized by the fact that $$K = \frac{\frac{Ct \text{ for pyruvate kinase gene}}{Ct \text{ for } COX_1 \text{ gene}} + \frac{Ct \text{ for } NC_{018923.2} \text{12th chromosome fragment}}{Ct \text{ for } COX_1 \text{ gene}}}{2}.$$

In particular case of implementation, the diagnostic method for a disease accompanied by the increased cell death is characterized by the fact that $$K = \frac{\frac{Ct \text{ for pyruvate kinase gene}}{Ct \text{ for } COX_1 \text{ gene}} + \frac{Ct \text{ for } M6PRBP \text{ gene}}{Ct \text{ for } COX_1 \text{ gene}}}{2}.$$

In particular case of implementation, the diagnostic method for a disease accompanied by the increased cell death is characterized by the fact that $$K = \frac{\frac{Ct \text{ for pyruvate kinase gene}}{Ct \text{ for } COX_1 \text{ gene}} + \frac{Ct \text{ for } NC_{018923.2} \text{12th chromosome fragment}}{Ct \text{ for } COX_1 \text{ gene}} + \frac{Ct \text{ for } M6PRBP \text{ gene}}{Ct \text{ for } COX_1 \text{ gene}}}{3}.$$

The task was solved by creation of kit to perform the above diagnostic method for a disease accompanied by the increased cell death, including at least a pair of oligonucleotide primers and oligonucleotide probe for detection, in order to determine Ct for gene coding for glycolysis enzyme, and a pair of oligonucleotide primers and oligonucleotide probe for detection, in order to determine Ct for mitochondrial gene In particular case of implementation, the invention kit is characterized by the fact that the gene coding for glycolysis enzyme is the gene coding for pyruvate kinase, and a pair of oligonucleotide primers and oligonucleotide probe for detection, in order to determine Ct for gene coding for pyruvate kinase, have sequences, which are homologous at least by 90% to SEQ ID NO:1, SEQ ID NO:2 and SEQ ID NO:3 sequences, respectively.

In particular case of implementation, the invention kit is characterized by the fact that the gene coding for glycolysis enzyme is the gene coding for pyruvate kinase, and a pair of oligonucleotide primers and oligonucleotide probe for detection, in order to determine Ct for gene coding for pyruvate kinase, have SEQ ID NO:1, SEQ ID NO:2, and SEQ ID NO:3 sequences, respectively.

In particular case of implementation, the invention kit is characterized by the fact that mitochondrial gene is COX1 gene, and a pair of oligonucleotide primers and oligonucleotide probe for detection, in order to determine Ct for COX1 gene have sequences, which are homologous at least by 90% to SEQ ID NO:10, SEQ ID NO:11 and SEQ ID NO:12 sequences, respectively.

In particular case of implementation, the invention kit is characterized by the fact that mitochondrial gene is COX1 gene, and a pair of oligonucleotide primers and oligonucleotide probe for detection, in order to determine Ct for COX1 gene have SEQ ID NO:10, SEQ ID NO:11 and SEQ ID NO:12 sequences, respectively.

In particular case of implementation, the invention kit is characterized by the fact that it additionally contains a pair of oligonucleotide primers and oligonucleotide probe for detection, in order to determine Ct for $NC_{018923.2}$ 12th chromosome fragment.

In particular case of implementation, the invention kit is characterized by the fact that a pair of oligonucleotide primers and oligonucleotide probe for detection, in order to determine Ct for $NC_{018923.2}$ 12th chromosome fragment, have sequences, which are homologous at least by 90% to SEQ ID NO:4, SEQ ID NO:5 and SEQ ID NO:6 sequences, respectively.

In particular case of implementation, the invention kit is characterized by the fact that a pair of oligonucleotide primers and oligonucleotide probe for detection, in order to determine Ct for $NC_{018923.2}$ 12th chromosome fragment have SEQ ID NO:4, SEQ ID NO:5 and SEQ ID NO:6 sequences, respectively.

In particular case of implementation, the invention kit is characterized by the fact that it additionally contains a pair of oligonucleotide primers and oligonucleotide probe for detection, in order to determine Ct for M6PRBP gene.

In particular case of implementation, the invention kit is characterized by the fact that a pair of oligonucleotide primers and oligonucleotide probe for detection, in order to determine Ct for M6PRBP gene, have sequences, which are homologous at least by 90% to SEQ ID NO:7, SEQ ID NO:8 and SEQ ID NO:9 sequences, respectively.

In particular case of implementation, the invention kit is characterized by the fact that a pair of oligonucleotide primers and oligonucleotide probe for detection, in order to determine Ct for M6PRBP gene have SEQ ID NO:7, SEQ ID NO:8 and SEQ ID NO:9 sequences, respectively.

In particular case of implementation, the invention kit is characterized by the fact that it additionally contains a pair of oligonucleotide primers and oligonucleotide probe for detection, in order to determine Ct for 12th chromosome fragment (43119006-43120809) and a pair of oligonucleotide primers and oligonucleotide probe for detection, in order to determine Ct for M6PRBP gene In particular case of implementation, the invention kit is characterized by the fact that it additionally contains reagents for isothermal amplification.

In particular case of implementation, the invention kit is characterized by the fact that the reagents for isothermal amplification include DNA polymerase phi29, protein binding with single straight DNA, trehalose, random primers, detergent, deoxynucleoside triphosphates, magnesium chloride.

In particular case of implementation, the invention kit is characterized by the fact that it additionally contains reagents for real-time polymerase chain reaction.

In particular case of implementation, the invention kit is characterized by the fact that the reagents for real-time polymerase chain reaction include thermostable DNA polymerase, buffer for the polymerase chain reaction, deoxynucleoside triphosphates.

Method and invention kit provide for achievement of technical result, that is the diagnostics of disease for a disease accompanied by the increased cell death; at that, the diagnostics is minimally invasive, has a high sensitivity at any stages of disease including early stages, at which the clinical signs are absent. Moreover, the method and invention kit can be used for the following:

Under differential diagnostics of benign and malignant tumors including at early stages, at which the clinical signs are still absent;

For quality control of treatment of diseases, with which the increased cell death takes place (treatment efficiency monitoring);

Under carrying out of clinical studies for new medicinal drugs;

For initial screening of patients for presence of diseases accompanied by the increased cell death in the body and appearance of nucleic acids in the human blood plasma.

The following terms and definitions are used in this Application.

Nucleic acids (NAs)—they include DNA (deoxyribonucleic acid), RNA (ribonucleic acid), mRNA (informational RNA, messenger RNA), small interfering RNA (microRNA), tRNA (transfer RNA), polynucleotides from cell organelles: nucleuses, mitochondrions, cytoplasm of cells, exosome, blood plasma or oligonucleotides synthesized in vitro. This term can mean both one type of NAs and mix of NAs different types: at that, contextually, a specialist in this field understands the meaning of this term.

Glycolysis—a metabolic pathway, in which glucose turns into pyruvate with the help of ten enzymes: hexokinase, phosphoglucose isomerase, phosphofructokinase, fructose biphosphate aldolase, triosephosphate isomerase, glyceraldehyde phosphate dehydrogenase, phosphoglycerate kinase, phosphoglycerate mutase, enolase, and pyruvate kinase.

Coefficient K –Ct ratio or average of Ct ratios between genomic DNA fragments and mitochondrial DNA fragment is determined as follows:

$$K = C_1 \text{ or } K = \frac{C_1 + C_2}{2}, \text{ or } K = \frac{C_1 + C_3}{2}, \text{ or } K = \frac{C_1 + C_2 + C_3}{3},$$

$$\text{where } C_1 = \frac{Ct \text{ for gene coding for glycolysis enzyme}}{Ct \text{ for mitochondrial gene}},$$

$$C_2 = \frac{Ct \text{ for } NC_{018923.2} \text{12th chromosome fragment}}{Ct \text{ for mitochondrial gene}},$$

$$C_3 = \frac{Ct \text{ for } M6PRBP \text{ gene}}{Ct \text{ for mitochondrial gene}},$$

The $12^{th}$ chromosome fragment—chr12 (43119006-43120809), NC_018923.2, (SEQ ID NO:13).

Author of this invention proved by experiments that the patients with diseases accompanied by the increased cell death have coefficient K <2.0. The healthy blood donors have coefficient K ≥2.0. At present, no exclusions from this regularity were revealed. That is why the Author of this invention named this coefficient as "coefficient of health" ($K_3$).

Ct—Analytical signal, threshold cycle, at which a value of the amplification cycle, on which the fluorescence due to segregation of the oligonucleotide probe for detection has exceeded a value of the background fluorescence.

Reference value of the laboratory parameter, in this case, of coefficient K —average value of the laboratory parameter, in this case, of coefficient K received during mass health examination.

The reagent kit for method performing—the reagent kit can be both "complete kit" and "incomplete kit". The "complete kit" is a complete reagent kit required to perform the stages of the invention method: sampling of human blood plasma, isothermic nucleic acids amplification of blood plasma, nucleic acids purification from the reaction mixtures, carrying out of nucleic acid quantification by real-time polymerase chain reaction method. The reagents required to perform each stage of the method are known to specialist in this technical field. The reagents for isothermic amplification include DNA polymerase phi29, protein binding with single straight DNA, trehalose, random primers, detergent, deoxynucleoside triphosphates, magnesium chloride. The reagents for real-time polymerase chain reaction include oligonucleotide primers, oligonucleotide probes for detection, thermostable DNA polymerase, buffer for the polymerase chain reaction, deoxynucleoside triphosphates. The thermostable DNA polymerase can be Taq-, Tth-, Tub-, Bst-, Vent-, Pfu-polymerase or other thermostable DNA polymerase known from the technical level. For example, SynTaq DNA polymerase with antibodies inhibiting the enzyme activity can be used. The "incomplete kit" is a reagent kit not including at least one ingredient of the complete kit, but including at least two pairs of the appropriate oligonucleotide primers and two appropriate oligonucleotide probes for detection.

Random primer—oligonucleotide primer (primer), nucleotide sequence of which is selected at random; it is used for amplification of nucleic acid fragments with unknown nucleotide sequence. The following synonyms can be used: scattered primer, random primer, non-specific primer. The random primers can be modified; for example, 7 nucleotide length random primers with 3"-S—S modification of Random-7 thio Syntol can be used.

The Author of this invention named the diagnostic method for a disease accompanied by the increased cell death as "ARNA" (Analysis of Ratio of Nucleic Acid).

The invention method consists of six consecutive stages, as follows: sampling of human blood plasma; isothermic nucleic acids amplification of blood plasma; nucleic acids purification from the reaction mixture obtained at the previous stage; carrying out of nucleic acid quantification by method of real-time polymerase chain reaction and determination of coefficient K in the samples; comparison of coefficient K with reference value; and actually the diagnostics of a disease accompanied by the increased cell death, if the value of coefficient K is less than the reference value.

Stage 1 Sampling of Human Blood Plasma

The human blood plasma is used for analysis. The blood can be taken from both vein and finger: only several drops of the blood required for selection into tube with preservative (for example, 10 mM concentration EDTA (ethylene diamine tetraacetate) or heparin). To prevent the cell decay, the tube with blood is kept at 4° C. up to centrifugation, and plasma shall be obtained from the blood not later than within 1 hour. The blood cell centrifugation is carried out at 1,000 g during 10 minutes. The upper layer is selected neatly without contact with interphase. Deviation of the procedure described results in the blood cell decay during the plasma extraction process and errors in the analysis. Prior to the analysis, the plasma is kept frozen at −20° C. up to 1 month, at −80° C. up to year.

Stage 2 Isothermic Nucleic Acids Amplification of Blood Plasma

This amplification is performed by DNA polymerase of bacteriophage phi29 without preliminary nucleic acids isolation from blood plasma and takes place in one tube, which is one of the essential features of the invention. It is crucially important, that the nucleic acids present in plasma at the moment of blood sampling from patient are taken for synthesis in tube without distortions, which occur under biochemical methods of nucleic acids isolation. It is known that when using ion-exchange columns, the nucleic acid fragments are binding differently depending on G-C composition. Such distortions occur at the nucleic acid precipitation stage, as the short fragments of nucleic acids (15-100 nucleotides) are precipitated with alcohols with lesser yield. The nucleic acid fragments from 7 nucleotides and more perform the priming function in amplification reaction. These parameters become essential when working with small quantities of nucleic acids, 1 ng and less.

The nucleic acids amplification is performed by DNA polymerase of phi29 (NEB, cat. #M0269L) in presence of protein binding with single straight DNA (NEB, SSB protein cat. #M0249S), trehalose, random primers (which are modified 7 nucleotide length oligonucleotides with 3'-S—S modification of Random-7 thio Syntol) resistant to exonuclease, detergent (for example, 8% polyethylene glycol, but other appropriate detergent can be used as well), deoxynucleoside triphosphates (dNTP), magnesium chloride and nucleic acids of human blood plasma (Table 1) and continues for 16 hours at 30° C.

TABLE 1

Incubation mixture composition for DNA synthesis

| Component | Volume |
|---|---|
| 10 × buffer | 10 µl |
| 1.35 mM trehalose | 28 µl |
| 25 mM dNTP | 10 µl |
| Random primers, 0.5 mM | 3 µl |
| 10 mg/ml BSA (bovine serum albumine) | 2 µl |
| 0.1M DTT (dithiothreitol) | 1 µl |
| Detergent (50% polyethylene glycol) | 8 µl |
| Blood plasma | 10 µl |
| Protein SSB | 1 µl/20 ng |
| Phi29 DNA polymerase | 5 µl/500 u |
| Water | Up to 100 µl |

For the nucleic acids denaturation, the mixture prepared is incubate for 2 minutes at 95° C., then the tubes are carried to ice, DNA polymerase with protein SSB is added, and incubation continues for 16 hours at 30° C. Table 1 shows the optimal component concentrations, which are sufficient for DNA synthesis up to 10 µg. Increase of concentration of enzyme of DNA polymerase of phi29, dNTP and random primers is able to increase the DNA yield, but DNA amount synthesized is sufficient for analysis and there is no need in the greater amount.

Stage 3 Nucleic Acids Purification from the Reaction Mixture

The third stage concludes in the synthesis stop and DNA purification. For synthesis stop, EDTA up to 10 mM, proteinase K up to 100 µg/ml are added for breakdown of all proteins within the reaction mixture, and incubation at 55° C. for 15 minutes is carried out.

The further purification is performed with two volumes of reagent DNAZOL BD (MRC, cat. #DN129), with precipitation by 1.2 volumes of isopropanol, additional washing of sediment with 80% ethanol, with the subsequent dilution in TE buffer and determination of the DNA concentration. The DNA concentration is determined using fluorometer with fluorescent paint Hoechst or spectrophotometer in terms of optical dense at 260/280 nm.

Stage 4 Carrying Out of Nucleic Acid Quantification by Real-Time Polymerase Chain Reaction (PCR) Method and Determination of Coefficient K in the Samples.

To carry out the nucleic acid quantification by real-time PCR method (qPCR, real-time PCR), DNA obtained at stage 3 is used. The quantification by PCR method is carried out as per Standard Protocol of Company Syntol (Syntol, cat #M-428). The detection is performed using probes TaqMan; the probes are selected as per recommendations of Company Biosearch Technologies Inc. the reaction mixture composition is shown in Table 2, the sequences of oligonucleotide primers and oligonucleotide probes for detection are shown in Table 3. It is clear for a specialist that this kit of the oligonucleotide primers and oligonucleotide probes for detection (quantity and sequences) is a non-limiting example of this group of inventions. DNA quantity, which equals to 50 ng, is optimal for ratio of the reagents specified in Table 2. DNA content used within the reaction can vary from several ng to 0.5 µg.

TABLE 2

Composition of incubation mixture for quantification by PCR method

| Component | Volume |
| --- | --- |
| 10 × buffer | 2.5 µl |
| Magnesium chloride, 25 mM | 2.5 µl |
| dNTP, 2 mM | 2.5 µl |
| Oligonucleotide primers, 10 pmol/µl each | 1 µl |
| Oligonucleotide probe for detection, 10 pmol/µl | 0.5 µl |
| SynTaq DNA polymerase with antibodies inhibiting the enzyme activity | 0.1 µl |
| DNA | 1-10 µl |
| Water | Up to 25 µl |

TABLE 3

Sequences of oligonucleotide primers and oligonucleotide probes for detection

| Number | DNA fragment | Function | Sequence* |
| --- | --- | --- | --- |
| SEQ ID NO: 1 | gene PKLR | primer | GTCAGGGCTGCTCTGGGT |
| SEQ ID NO: 2 | pyruvate kinase, | primer | TCACGCCTTCGTGGTTCTC |
| SEQ ID NO: 3 | glycolysis enzyme | probe | 5'FAM-CCGGAAGGACACGGCATCAAGA-3'BHQ1 |
| SEQ ID NO: 4 | fragment of 12th | primer | TGCCGTCAACTCTCCAGTAAAC |
| SEQ ID NO: 5 | chromosome of | primer | CCTGCAGCTGGCTTCTCAAAG |
| SEQ ID NO: 6 | NC_018923.2 chr12 (43119006-43120809) | probe | 5'FAM-CGCTCTCTGTTGCTGCCAGGAA-3'BHQ1 |
| SEQ ID NO: 7 | M6PRBP gene | primer | CGGTCACTACGGACTTTGTC |
| SEQ ID NO: 8 | | primer | ACCAAGGAGCTTGTGTCGTCTAAG |
| SEQ ID NO: 9 | | probe | 5'FAM-TGTCCTTGGCGCTAGACACCA-3'BHQ1 |
| SEQ ID NO: 10 | COX1 gene | primer | CAAACCACAAAGACATTGGAACACT |
| SEQ ID NO: 11 | mitochondrial | primer | CAGCTCGGCTCGAATAAGGA |
| SEQ ID NO: 12 | gene | probe | 5'FAM-ATTCGGCGCATGAGCTGGAGTC-3'BHQ1 |

*Fluorescence dye and fluorescence extinguisher are given in addition for the probes
qPCR scheme is as the following:

95° C./5 min + (95° C./15 s + 62° C./20 s + 72° C./45 s) × 40 cycles.

Based on Ct values obtained, coefficient К is determined in the samples:

$$K = C_1 \text{ or } K = \frac{C_1 + C_2}{2}, \text{ or } K = \frac{C_1 + C_3}{2}, \text{ or } K = \frac{C_1 + C_2 + C_3}{3},$$

$$\text{where } C_1 = \frac{Ct \text{ for gene coding for glycolysis enzyme}}{Ct \text{ for mitochondrial gene}},$$

$$C_2 = \frac{Ct \text{ for } NC_{018923.2} \text{ 12th chromosome fragment}}{Ct \text{ for mitochondrial gene}},$$

$$C_3 = \frac{Ct \text{ for } M6PRBP \text{ gene}}{Ct \text{ for mitochondrial gene}}.$$

Stages 5 and 6 Comparison of coefficient К with reference value and diagnostics of a disease accompanied by the increased cell death with coefficient К value less than the reference value Diagnostics of a Disease Accompanied by the Increased Cell Death-Breast Cancer Using the above invention method, the blood plasma samples taken from both healthy donors and patients with breast cancer were analyzed. The samples were obtained from Cancer Center named after Blokhin (Moscow city). Age of the women varied from 29 to 79 years. As is seen from data given in Table 4, the invention method and kit for its performing allow to distinguish reliably the plasma of healthy donors from that of patients with breast cancer regardless of the disease stage. The method sensitivity is sufficient for the disease recognition at $1^{st}$ stage as well.

$$\text{Coefficient } \kappa = \frac{\dfrac{Ct \text{ for pyruvate kinase gene}}{Ct \text{ for } COX_1 \text{ gene}} + \dfrac{Ct \text{ for } NC_{018923.2} \text{12th chromosome fragment}}{Ct \text{ for } COX_1 \text{ gene}} + \dfrac{Ct \text{ for } M6PRBP \text{ gene}}{Ct \text{ for } COX_1 \text{ gene}}}{3}$$

of patients varies from 1.2 to 1.6. In samples BC24 and BC35, coefficient is equal to 1.9; the blood for analysis was taken from these patients after the surgical operation. All healthy donors have coefficient exceeding or equal to 2.0. (K >2.0). The method's accuracy is ±0.1. The mathematical error of analysis p (po) was calculated; for most samples it varies within 1/10,000-1/1,000 interval; it demonstrates the method reliability. Use of other statistical methods for processing of the data obtained is possible.

For all samples given in Table 4, the coefficients were determined as well, as follows:

$$\frac{Ct \text{ for pyruvate kinase gene}}{Ct \text{ for } COX_1 \text{ gene}},$$

$$\frac{\dfrac{Ct \text{ for pyruvate kinase gene}}{Ct \text{ for } COX_1 \text{ gene}} + \dfrac{Ct \text{ for } M6PRBP \text{ gene}}{Ct \text{ for } COX_1 \text{ gene}}}{2} \text{ and}$$

$$\frac{\dfrac{Ct \text{ for pyruvate kinase gene}}{Ct \text{ for } COX_1 \text{ gene}} + \dfrac{Ct \text{ for } NC_{018923.2} \text{12th chromosome fragment}}{Ct \text{ for } COX_1 \text{ gene}}}{2}.$$

At that, what is worthy of note, the regularity remained the same, as follows: patients with breast cancer have always had coefficients K less than 2.0; healthy blood donors have always had coefficients K more than 2.0 or equal to 2.0.

Thus, based on the data obtained, it is possible to state that the invention method and kit allow to recognize a disease accompanied by the increased cell death—breast cancer with sensitivity>97% at all stages of the disease development (0 errors with sampling 27 of truly positive samples).

TABLE 4

Values of $\kappa = \dfrac{\dfrac{Ct \text{ for pyruvate kinase gene}}{Ct \text{ for } COX_1 \text{ gene}} + \dfrac{Ct \text{ for } NC_{018923.2}\text{12th chromosome fragment}}{Ct \text{ for } COX_1 \text{ gene}} + \dfrac{Ct \text{ for } M_6PRBP \text{ gene}}{Ct \text{ for } COX_1 \text{ gene}}}{3}$ and $\rho$ for healthy donors and patients with breast cancer

| # | Healthy donors | κ | ρ | Patients with breast cancer | κ | ρ | Stage of disease |
|---|---|---|---|---|---|---|---|
| 1 | D1 | 3.9 | 1.63E−04 | BC2 | 1.5 | 4.00E−04 | 1 |
| 2 | D2 | 2.2 | 1.19E−03 | BC4 | 1.6 | 4.00E−04 | 1 |
| 3 | D3 | 3.7 | 1.63E−04 | BC5 | 1.5 | 4.00E−04 | 1 |
| 4 | D4 | 5.0 | 1.63E−04 | BC6 | 1.5 | 4.00E−04 | 1 |
| 5 | D5 | 4.2 | 1.63E−04 | BC7 | 1.6 | 4.00E−04 | 1 |
| 6 | D6 | 3.3 | 1.63E−04 | BC1 | 1.5 | 4.00E−04 | 2A |
| 7 | D7 | 3.2 | 1.63E−04 | BC8 | 1.6 | 4.00E−04 | 2A |
| 8 | D8 | 3.2 | 1.63E−04 | BC9 | 1.6 | 2.74E−03 | 2A |
| 9 | D9 | 2.4 | 1.63E−04 | BC12 | 1.5 | 4.00E−04 | 2A |
| 10 | D10 | 2.5 | 1.19E−03 | BC13 | 1.6 | 2.74E−03 | 2A |
| 11 | D11 | 2.3 | 1.63E−04 | BC10 | 1.6 | 5.55E−03 | 2A |
| 12 | D12 | 3.4 | 1.63E−04 | BC11 | 1.2 | 4.00E−04 | 2A |
| 13 | D13 | 2.5 | 1.63E−04 | BC14 | 1.4 | 4.00E−04 | 2A |
| 14 | D14 | 2.2 | 1.19E−03 | BC25 | 1.4 | 4.00E−04 | 2A |
| 15 | D15 | 3.0 | 1.63E−04 | BC3 | 1.3 | 4.00E−04 | 3B |
| 16 | D16 | 2.3 | 1.63E−04 | BC15 | 1.4 | 4.00E−04 | 3 |
| 17 | D17 | 2.9 | 1.63E−04 | BC36 | 1.6 | 4.00E−04 | Prior to surgery |
| 18 | D18 | 2.7 | 1.63E−04 | BC37 | 1.5 | 4.00E−04 | Prior to surgery |
| 19 | D19 | 3.0 | 1.63E−04 | BC38 | 1.5 | 4.00E−04 | Prior to surgery |
| 20 | D20 | 2.6 | 4.76E−03 | BC39 | 1.6 | 4.00E−04 | Prior to surgery |
| 21 | D21 | 2.2 | 1.19E−03 | BC16 | 1.6 | 2.74E−03 | Prior to surgery |
| 22 | D22 | 3.0 | 1.63E−04 | BC20 | 1.3 | 4.00E−04 | After surgery |
| 23 | D24 | 3.7 | 1.63E−04 | BC24 | 1.9 | 3.70E−02 | After surgery + chemical therapy |
| 24 | D27 | 2.9 | 1.63E−04 | BC29 | 1.5 | 4.00E−04 | After surgery - 2A |
| 25 | Dp1 | 2.2 | 1.63E−04 | BC32 | 1.6 | 4.00E−04 | After surgery |
| 26 | Dp2 | 2.0 | 1.63E−04 | BC34 | 1.6 | 4.00E−04 | After surgery - 2A |
| 27 | Dp3 | 2.3 | 1.63E−04 | BC35 | 1.9 | 4.00E−04 | After surgery - 2B |
| 28 | Dp4 | 2.4 | 1.63E−04 | | | | |
| 29 | Dp6 | 2.7 | 1.63E−04 | | | | |

Diagnostics of a Disease Accompanied by the Increased Cell Death—Hepatosis and Treatment Efficiency Monitoring Using the above invention method, the blood plasma sample taken from finger of volunteer M-33 having no clinical signs of any disease was analyzed. Unexpectedly, the volunteer's blood test revealed the following:

$$\kappa = \frac{\frac{Ct \text{ for pyruvate kinase gene}}{Ct \text{ for } COX_1 \text{ gene}} + \frac{Ct \text{ for } NC_{018923.2} \text{12th chromosome fragment}}{Ct \text{ for } COX_1 \text{ gene}} + \frac{Ct \text{ for } M6PRBP \text{ gene}}{Ct \text{ for } COX_1 \text{ gene}}}{3} = 1.3.$$

Two repeated analyses revealed the same result. In one of clinic, the physicians diagnosed hepatosis of liver for this volunteer and recommended him the treatment. After two months following the commencement of the treatment, the blood test revealed the efficiency of the treatment and return of coefficient to norm (K =2.5) (please, refer to Table 5).

TABLE 5

Change of coefficient $$\kappa = \frac{\frac{Ct \text{ for pyruvate kinase gene}}{Ct \text{ for } COX_1 \text{ gene}} + \frac{Ct \text{ for } NC_{018923.2} \text{12th chromosome fragment}}{Ct \text{ for } COX_1 \text{ gene}} + \frac{Ct \text{ for } M_6PRBP \text{ gene}}{Ct \text{ for } COX_1 \text{ gene}}}{3}$$

under treatment of patient with hepatosis

| Date | κ | Notes |
|---|---|---|
| May 23, 2014 | 1.3 | |
| May 26, 2014 | 1.4 | |
| May 26, 2014 | 1.3 | Diagnosing - hepatosis of liver |
| Feb. 13, 2015 | 1.3 | Commencement of treatment |
| Apr. 6, 2015 | 1.6 | |
| Apr. 13, 2015 | 2.5 | |

This example demonstrates a possibility to use the invention method and kit for diagnostics of a disease accompanied by the increased cell death—hepatosis at early stages, at which the clinical signs are absent, as well as for the treatment efficiency monitoring.

---

The invention claimed is:

1. A diagnostic method for breast cancer, the method comprising the steps of:
   a) sampling human blood plasma from a patient;
   b) amplifying isothermic nucleic acids of the human blood plasma;
   c) purifying nucleic acids from a reaction mixture produced in item b);
   d) quantifying nucleic acids by a real-time polymerase chain reaction method and determining a coefficient K :

$$K = \frac{C_1 + C_2 + C_3}{3},$$

Where $C_1 = \dfrac{Ct \text{ for gene coding for pyruvate kinase}}{Ct \text{ for } COX_1 \text{ gene}}$, $C_2 = \dfrac{Ct \text{ for } NC_{018923.2} \text{12th chromosome fragment}}{Ct \text{ for } COX_1 \text{ gene}}$, and -continued $$C_3 = \frac{Ct \text{ for } M6PRBP \text{ gene}}{Ct \text{ for } COX_1 \text{ gene}}, \text{ and}$$

wherein Ct is a value of a polymerase chain reaction threshold cycle of each of gene coding for pyruvate kinase, COX1 gene, $NC_{018923.2}$ 12th chromosome fragment, and M6PRBP gene; and e) comparing the coefficient K with a reference value to determine whether the coefficient K value is less than the reference value to diagnose breast cancer in the patient;

f) wherein the reference value is determined as average of coefficient K, received with healthy population screening, and the reference value is equal to 2.

2. The diagnostic method for breast cancer of claim 1, wherein the amplifying isothermic nucleic acids is carried out without preliminary isolating nucleic acids from the human blood plasma in a same tube with the human blood plasma.

3. The diagnostic method for breast cancer of claim 1, wherein the amplifying isothermic nucleic acids is carried out in a presence of DNA polymerase phi29.

4. The diagnostic method for breast cancer of claim 3, wherein the amplifying isothermic nucleic acids amplification of blood plasma is carried out in a presence of protein binding with single straight DNA, trehalose, random primers, detergents, deoxynucleoside triphosphates, and magnesium chloride.

5. The diagnostic method for breast cancer of claim 1, wherein the amplifying isothermic nucleic acids is stopped by adding ethylene diamine tetraacetate addition into the reaction mixture and then extracting the DNA.

6. The diagnostic method for breast cancer of claim 5, wherein extracting the DNA comprises the steps of: adding proteinase K into the reaction mixture, incubating the reaction mixture for 15 minutes at 55° C., processing the reaction mixture with a reagent for isolation of genomic DNA, precipitating DNA with isopropanol, and washing DNA with ethanol.

7. The diagnostic method for breast cancer of claim 6 further comprising dissolving the DNA extracted within a TE buffer and determining a concentration of the DNA extracted.

8. The diagnostic method for breast cancer of claim 1, wherein Ct for pyruvate kinase gene is determined using a pair of oligonucleotide primers and oligonucleotide probe for detection; at that, one oligonucleotide primer has a sequence, which is homologous at least by 90% to SEQ ID NO:1 sequence, the second oligonucleotide primer has a sequence, which is homologous at least by 90% to SEQ ID NO:2 sequence, the oligonucleotide probe for detection has a sequence, which is homologous at least by 90% to SEQ ID NO:3 sequence.

9. The diagnostic method for breast cancer of claim 1, wherein Ct for pyruvate kinase gene is determined using a pair of oligonucleotide primers and oligonucleotide probe for detection; at that, one oligonucleotide primer has SEQ ID NO:1 sequence, the second oligonucleotide primer has SEQ ID NO:2 sequence, the oligonucleotide probe for detection has SEQ ID NO:3 sequence.

10. The diagnostic method for breast cancer of claim 1, wherein Ct for $NC_{018923.2}$ 12th chromosome fragment is determined using a pair of oligonucleotide primers and oligonucleotide probe for detection; at that, one oligonucleotide primer has a sequence, which is homologous at least by 90% to SEQ ID NO:4 sequence, the second oligonucleotide primer has a sequence, which is homologous at least by 90% to SEQ ID NO:5 sequence, the oligonucleotide probe for detection has a sequence, which is homologous at least by 90% to SEQ ID NO:6 sequence.

11. The diagnostic method for breast cancer of claim 1, wherein Ct for $NC_{018923.2}$ 12th chromosome fragment is determined using a pair of oligonucleotide primers and oligonucleotide probe for detection; at that, one oligonucleotide primer has SEQ ID NO:4 sequence, the second oligonucleotide primer has SEQ ID NO:5 sequence, the oligonucleotide probe for detection has SEQ ID NO:6 sequence.

12. The diagnostic method for breast cancer of claim 1, wherein Ct for M6PRBP gene is determined using a pair of oligonucleotide primers and oligonucleotide probe for detection; at that, one oligonucleotide primer has a sequence, which is homologous at least by 90% to SEQ ID NO:7 sequence, the second oligonucleotide primer has a sequence, which is homologous at least by 90% to SEQ ID NO:8 sequence, the oligonucleotide probe for detection has a sequence, which is homologous at least by 90% to SEQ ID NO:9 sequence.

13. The diagnostic method for breast cancer of claim 1, wherein Ct for M6PRBP determined using a pair of oligonucleotide primers and oligonucleotide probe for detection; at that, one oligonucleotide primer has SEQ ID NO:7 sequence, the second oligonucleotide primer has SEQ ID NO:8 sequence, the oligonucleotide probe for detection has SEQ ID NO:9 sequence.

14. The diagnostic method for breast cancer of claim 1, wherein Ct for COX1 gene is determined using a pair of oligonucleotide primers and oligonucleotide probe for detection; at that, one oligonucleotide primer has a sequence, which is homologous at least by 90% to SEQ ID NO:10 sequence, the second oligonucleotide primer has a sequence, which is homologous at least by 90% to SEQ ID NO:11 sequence, the oligonucleotide probe for detection has a sequence, which is homologous at least by 90% to SEQ ID NO:12 sequence.

15. The diagnostic method for breast cancer of claim 1, wherein Ct for COX1 gene is determined using a pair of oligonucleotide primers and oligonucleotide probe for detection; at that, one oligonucleotide primer has SEQ ID NO:10 sequence, the second oligonucleotide primer has SEQ ID NO:11 sequence, the oligonucleotide probe for detection has SEQ ID NO:12 sequence.

16. The diagnostic method for breast cancer, wherein the oligonucleotide probe for detection contains fluorescent dye at 5"-end, fluorescence extinguisher at 3"-end.

* * * * *

SEQUENCE LISTING

<160> NUMBER OF SEQ ID NOS: 13

<210> SEQ ID NO 1
<211> LENGTH: 18
<212> TYPE: DNA
<213> ORGANISM: Homo Sapiens

<400> SEQUENCE: 1
gtcagggctg ctctgggt                                                 18

<210> SEQ ID NO 2
<211> LENGTH: 19
<212> TYPE: DNA
<213> ORGANISM: Homo Sapiens

<400> SEQUENCE: 2
tcacgccttc gtggttctc                                                19

<210> SEQ ID NO 3
<211> LENGTH: 22
<212> TYPE: DNA
<213> ORGANISM: Homo Sapiens

<400> SEQUENCE: 3
ccggaaggac acggcatcaa ga                                            22

<210> SEQ ID NO 4
<211> LENGTH: 22
<212> TYPE: DNA
<213> ORGANISM: Homo Sapiens

<400> SEQUENCE: 4
tgccgtcaac tctccagtaa ac                                            22

<210> SEQ ID NO 5
<211> LENGTH: 21
<212> TYPE: DNA
<213> ORGANISM: Homo Sapiens

<400> SEQUENCE: 5
cctgcagctg gcttctcaaa g                                          21

<210> SEQ ID NO 6
<211> LENGTH: 22
<212> TYPE: DNA
<213> ORGANISM: Homo Sapiens

<400> SEQUENCE: 6
cgctctctgt tgctgccagg aa                                         22

<210> SEQ ID NO 7
<211> LENGTH: 20
<212> TYPE: DNA
<213> ORGANISM: Homo Sapiens

<400> SEQUENCE: 7
cggtcactac ggactttgtc                                            20

<210> SEQ ID NO 8
<211> LENGTH: 24
<212> TYPE: DNA
<213> ORGANISM: Homo Sapiens

<400> SEQUENCE: 8
accaaggagc ttgtgtcgtc taag                                       24

<210> SEQ ID NO 9
<211> LENGTH: 21
<212> TYPE: DNA
<213> ORGANISM: Homo Sapiens

<400> SEQUENCE: 9
tgtccttggc gctagacacc a                                          21

<210> SEQ ID NO 10
<211> LENGTH: 25
<212> TYPE: DNA
<213> ORGANISM: Homo Sapiens

<400> SEQUENCE: 10
caaaccacaa agacattgga acact                                      25

<210> SEQ ID NO 11
<211> LENGTH: 20
<212> TYPE: DNA
<213> ORGANISM: Homo Sapiens

<400> SEQUENCE: 11
cagctcggct cgaataagga                                            20

<210> SEQ ID NO 12
<211> LENGTH: 22
<212> TYPE: DNA
<213> ORGANISM: Homo Sapiens

<400> SEQUENCE: 12
attcggcgca tgagctggag tc                                         22

<210> SEQ ID NO 13
<211> LENGTH: 1804
<212> TYPE: DNA

<213> ORGANISM: Homo Sapiens

<400> SEQUENCE: 13

```
aatgaaatga atgacaaagt cccctaaaat aactatcagg gtctcctccc tccacagtgg    60
aggagcccct ctctgtctca tgcttctctg acatggtctg cacatgctgc tggttgggtg   120
tgaagttagt atcctaggca gaagagtgaa ttgacaactt tatatgtttt caagttgttt   180
aaagtataaa ccactttagc gatggatctt ggaatggttg aaattgtggt ttgtgaaata   240
agcacttaat ttaagattgg aaatacccac aggaataact gagcctataa aatatgaaaa   300
ttcacatcaa cctgtaatga taaacatata tgaagtacac aacctgtaaa gataagagta   360
tatcacatca acctgtaatg ataaaagtat atgaagtaca caaaagcatg acttgagttt   420
acaagacttg tccagagagc acagaaaatc acgtgctact gggtaattca gacaaatagc   480
tttggcttgc ccttaattac ctaaacaatt caggactgag ctgggccatt tttaactgaa   540
tataattagg gtggttccct ttggttgtgt ggacctgggt atataatatg ttgtatttca   600
attcctataa tttacaggca tatgagcagg ctaaatattg taaagcagga tatggttcct   660
ggaggatgcc agcatccacc cactaattga cctgctaaga accagcagca acatgctctc   720
cagttgtggt ctggaggctg aattacaata aatacccaca tgagtgtctt atttagattt   780
gtccgattaa aaaaactcat gtacaaagct gatgagacct atgttagttg caggttaata   840
cttgctgatt tcttgccgtc aactctccag taaacaagaa cgaaggcatg gccaggcgct   900
ctctgttgct gccaggaagg gaggctttga gaagccagct gcagggcagg ggcatggcca   960
ggagcattgg tcttggagcc agataatttg ggttgcactc tttgtttgga tacttctctt  1020
cctttgaccc ttcgtcactt atggaagcta gaccacagtt ttctcatctg caaaatagag  1080
gcaatgatgt ggttctcaca gatggttgtg agatacaagg cggcaaggtt tgagactgct  1140
ccttataatt aagtcgttgg catagaggaa aagactggtg tttgcaatcc ctttactagg  1200
cagcatcttg gtgggaattc tgagaaagga cccagtgagc ctatggccag tctcctccaa  1260
cttgggatgg tgtctagatt ccaaacaaag agccagtggg cagcagaaaa gcaaagcact  1320
ggtttctgac tgaggggcca ttgggccccc cgtgggagac agatctttaa taatgttttt  1380
aatgacagtt cctttccaat gtgggggaag tctgtactga gagaaactcg atgcctctgg  1440
cctcgggcgg cagaattacc atgtatcttt taatctcaag gaataaggag ctttagttca  1500
caacaaccct gtgcatcttg tctaggcctc ctgctacact gtgttcaggt aatcacatca  1560
aatggagaaa tcagatagtt tctggctgat tcaaaatgtc ctggctgaga ggcagaggag  1620
atgtcaacag agatttcagg ctcatggaaa aacgctcagg tccagcttca tctgcttgtt  1680
ccattctaat cagagaggtc ctctgtgggt cgtaagacaa gaaactaggg gtttaaaggt  1740
ccctcaggaa ccagggacca aaatctggat ctgaggagca aaatgcttaa acaagctctg  1800
tctg                                                               1804
```